(12) United States Patent
Padula

(10) Patent No.: US 8,567,950 B2
(45) Date of Patent: Oct. 29, 2013

(54) APPARATUS FOR TREATING VISUAL FIELD LOSS

(76) Inventor: William V. Padula, Guilford, CT (US)

( * ) Notice: Subject to any disclaimer, the term of this patent is extended or adjusted under 35 U.S.C. 154(b) by 35 days.

(21) Appl. No.: 12/653,139

(22) Filed: Dec. 9, 2009

(65) Prior Publication Data

US 2010/0171926 A1    Jul. 8, 2010

Related U.S. Application Data

(60) Provisional application No. 61/201,695, filed on Dec. 12, 2008.

(51) Int. Cl.
*A61B 3/02* (2006.01)
*A61B 3/00* (2006.01)
*A61B 3/024* (2006.01)

(52) U.S. Cl.
CPC .................................. *A61B 3/024* (2013.01)
USPC ........................ 351/224; 351/226; 351/246

(58) Field of Classification Search
USPC .................... 351/202, 203, 224, 226, 246
See application file for complete search history.

(56) References Cited

U.S. PATENT DOCUMENTS 7,549,743 B2 * 6/2009 Huxlin et al. ............. 351/203

* cited by examiner

*Primary Examiner* — Jack Dinh
(74) *Attorney, Agent, or Firm* — DLA Piper LLP (US)

(57) ABSTRACT

A method and apparatus for treating visual field loss by disassociating and differentiating between the ambient and focal visual information of a patient. This is achieved by providing a stationary target for the patient to focus on and a moving, spinning or rotating background relative to the stationary target.

11 Claims, 2 Drawing Sheets

APPARATUS FOR TREATING VISUAL FIELD LOSS

I. CROSS REFERENCE TO RELATED APPLICATIONS

Figure 1:
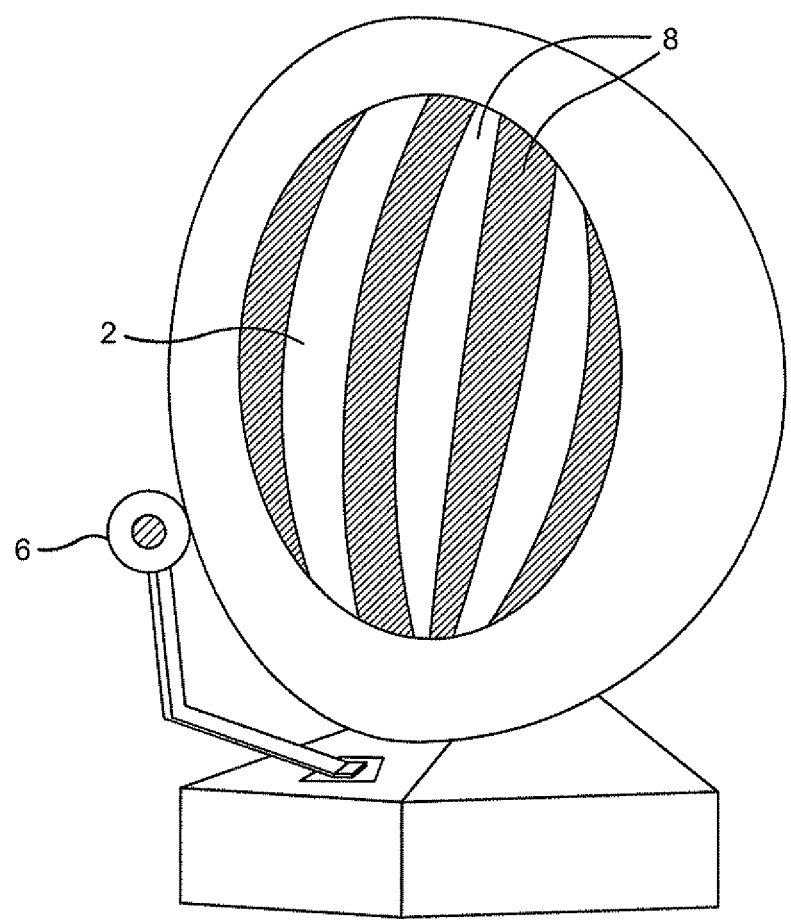

None.

II. STATEMENT REGARDING FEDERALLY SPONSORED RESEARCH OR DEVELOPMENT

None.

III. PARTIES TO A JOINT RESEARCH AGREEMENT

None.

IV. REFERENCE TO SEQUENCE LISTING

None.

V. BACKGROUND OF THE INVENTION

1. Field of Invention a. The present invention relates to method and apparatuses for treating persons with visual mid-line shift syndrome, vertigo, dizziness and spatial dysfunction causing difficulty with mobility, ambulation and driving of an automobile.

2. Introduction

Persons incurring neurologic events such as a traumatic brain injury (TBI) or Cerebrovascular accident (CVA) can result in visual field loss. The field loss will often be projected to the same field of view for each eye. This means that a neurological event affecting the right cerebral cortex will cause a field loss in the left field of both eyes. This is termed a left homonymous hemianopsia. A lesion affecting the left cerebral cortex will produce a field loss for each eye on the right side. This is termed a right homonymous hemianopsia.

This type of vision impairment will cause significant interference in function and performance. Homonymous hemianopsias will directly affect spatial orientation, posture and balance. Persons with this resultant condition will frequently bump into objects on one side and are more susceptible to injury from trauma or falls. This is due to the homonymous hemianopsia causing a Visual Midline Shift Syndrome (VMSS) which affects the concept of the ego center or visual midline in addition to the blind spot produced by the field loss. Also, it causes reading to become very difficult because right homonymous hemianopsia causes a spatial visual field loss which blocks the next word to be read. Consequently, a left homonymous hemianopsia causes difficulty in shifting gaze from the end of the line of print on the right side to the beginning of the next line of print.

In addition, homonymous hemianopsia interferes with daily living skills. Activities such as shopping in a store, conversing in a group of people, and even finding food on the plate will become very challenging. In turn, homonymous hemianopsia will affect socialization and reduce independence. A person with a homonymous hemianopsia is most often not safe to drive. This will in turn affect employment, earning potential, family relationships, to name several.

Homonymous hemianopsia can be determined behaviorally as well as clinically. Behaviorally, a person with a homonymous hemianopsia will have spatial difficulties causing bumping into objects, drifting when walking and/or not seeing objects on the side of the field loss. Clinically doctors will perform a visual field test to diagnose the condition. There are many different types of manual as well as automated visual field tests that require a response from the patient. All tests utilize a monocular assessment and require that the patient hold his or her fixation steady on a target. The standard automated instrument then projects sequential isolated lights that are timed to be presented in the peripheral field of the patient. The patient then presses a button each time he/she sees the light. The instrument then maps the visual field and corresponding field loss for each eye.

Research has shown that the visual system is composed of at least two processes. The focal visual process is primarily a function of the occipital cortex is oriented towards details related to higher cognitive process for attention. The second process is ambient and spatial in nature. Rather than being central in origin, it is mediated by the peripheral section and information is relayed through axons to the mid brain. It is here that information about a potential context (vertical and horizontal lines and boundaries in the peripheral field as well as orientation of the plane of the floor) is matched with sensory-motor information from the kinesthetic, proprioceptive and vestibular systems for organization of balance, posture and movements. This process organizes this information much faster than the focal process and before the detail is deceived the ambient process feed-forwards spatial information to 99% of the cortex willing the occipital cortex where the focal visual process functions.

Following a neurological event such as a TBI, CVA, etc. dysfunction can occur interfering with the ambient spatial visual process. This leaves the focal visual process to isolate on detail without the spatial context from the ambient system. In turn, the affected focal visual process attempts to function, but it lacks the ability to adapt to changes and becomes bound on details.

It is the ambient visual process that releases the focal process form isolation. Also, the ambient visual process is continually anticipating change and acts as a balance against isolation or over-focalization on detail. Dysfunction between these processes causes slow reaction time and an inability to adapt to environmental changes. This condition has been called Post Trauma Vascular Syndrome (PTVS).

VI. SUMMARY OF THE INVENTION

It is a general object of the present invention to provide a method and apparatuses for treating visual field loss as a result of traumatic brain injury (TVI) or cerebrovascular accident (CVA).

It is another object of the invention to provide method and apparatuses for treating persons with vertigo, dizziness and spatial dysfunction causing difficulties with mobility, ambulation and driving of an automobile.

The above invention features an object of the present invention can be accomplished by methods and apparatuses to disassociate and differentiate between ambient and focal visual information. Such methods and apparatuses include providing a target on which a patient focuses and which appears to be stationary while also providing a background which moves, rotates or spins relative to the stationary target on which the patient's attention is focused.

VII. BRIEF DESCRIPTION OF THE DRAWINGS

Figure 2:
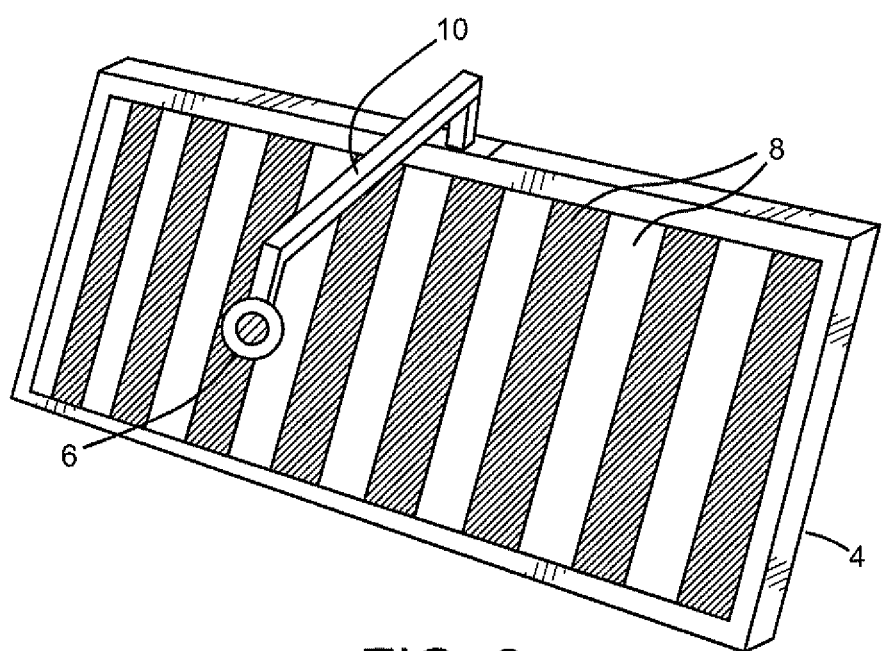

The above mentioned features and objects of the present invention will become more apparent with reference to the following description taken in conjunction with the accompanying drawings wherein like numerals denote like elements and in which:

FIG. 1 is one embodiment of the present invention; and
FIG. 2 is a second embodiment of the present invention.

VIII. DETAILED DESCRIPTION OF THE INVENTION

I have found clinically that when a person with dysfunction between the ambient and focal process is given an automated visual field test, they often have a difficult time keeping up with the timing of the lights presented and the lights presented in the area of field that is affected will demonstrate a visual field loss on one side.

However, from my research and clinical studies I have recognized that visual field testing presents details and when there is dysfunction of the ambient spatial visual process, the focal system fails to discern the stimulus (the lights presented in the involved visual field). This is caused by a compression of ambient space on the side of the field loss.

I have determined that if prisms are placed with the base end (thick end) oriented in the direction of the field and the subject is given activities to dissociate and differentiate between ambient and focal visual information, many subjects will report seeing the room on the side of their field loss. A series of therapeutic activities have been developed that will cause the ambient visual process to reorganize. The activities incorporate the use of parallax to dissociate the focal process from the ambient process. An activity named "Orbit" has been found to be effective. It involves suspending an abject in the middle of the room having the person with homonymous hemianopsia walk in a circumference around the target. The focalization on the target in the center of the circle that is walked appears stationary, but the room will appear to rotate or spin in the background behind the target in the opposite direction than the subject is walking.

At first the subject may report seeing the room and movement only on the side of the room related to the open visual field. The room appears to begin at the target and is seen only to one side of the target.

With repetition the prism in combination with the activity causes the ambient visual process to be differentiated separate from the focalization and subjects will report seeing the room on the other side of the target. At first, the room may appear compressed and the movement of the room may appear to move faster on the affected side than the non-affected side. With repetition, I have found that the field and movement will expand and slow down to match the field on the non-affected side enabling the subject to see more of the room or even the entire room in the scope of the field projected from their eyes.

Over time I have found that the field for many persons will open because the ambient visual process becomes functional as a spatial system supporting focalization. It is my opinion that the present mode of visual field testing may be ineffective and inaccurate for assessment of dysfunction between the ambient and focal visual process. In turn, present automated field instruments may produce false negative results. Some persons actually report seeing the whole room, yet the automated instruments (perimeters) show a homonymous hemianopsia.

Another means which is found to be effective is to have a person sit in front of a curved screen 2 of a shell or spherical monitor (FIG. 1) or a flat screen 4 of a flat monitor (FIG. 2) with black and white or contrasting colored stripes 8 moving from right to left or to the right. The stripes move past a central fixation target 6 that may be on the screen or in front of it supported on a telescopic boom 10. As the person focalizes on the target 6, the person will begin to see the stripes moving in the affected field. The contrast sensitivity can be adjusted by reducing the width of the stripes from low spatial frequency (wide stripes) to high spatial frequency (narrow stripes). The black and white stripes 8 can be generated by connection software created by one of ordinary skill in the art running on a personal computer (not shown) coupled to the monitor.

These procedures and use of related instruments have also been found to be effective for treating persons with vertigo, dizziness and spatial dysfunction causing difficulty with mobility, ambulation and driving an automobile.

It should be apparent to one of ordinary skill in the art that the above described embodiments represent but a few possible embodiments of the present invention and numerous other embodiments could be made without departing from the spirit and scope of the invention.

The invention claimed is:

1. A method for treating visual field loss comprising the steps of:
   providing a stationary target for a patient to focus on; and
   providing a background for the stationary target separate from and behind the stationary target, said background moving relative to said stationary target while said patient simultaneously views said relatively moving background and said stationary target whereby ambient and focal visual information of the patient are disassociated and differentiated by said patient simultaneously viewing said stationary target and said relatively moving background.

2. The method according to claim 1, wherein said relatively moving background is provided by having the patient walk around the stationary target in a circle.

3. The method according to claim 1, wherein said relatively moving background is provided by moving a plurality of contrasting stripes across a monitor.

4. The method according to claim 1 wherein said relative motion of said stationary target and said relatively moving background is selected from the group consisting of horizontal, spinning and rotational movement.

5. The method according to claim 1 wherein the stationary target is not provided in a same plane as said moving background.

6. An apparatus for treating visual field loss comprising:
   a stationary target for a patient to focus on; and
   a means for providing a background for the stationary target separate from and behind said stationary target, said background moving relative to said stationary target for said patient to simultaneously view said stationary target and said relatively moving background whereby ambient and focal visual information of the patient are disassociated and differentiated by said patient simultaneously viewing said stationary target and said relatively moving background.

7. The apparatus according to claim 6, wherein said means for providing said relatively moving background comprises a monitor provided with a plurality of moving contrasting stripes.

8. The apparatus according to claim 7, wherein said monitor comprises a shell monitor.

9. The apparatus according to claim 7, wherein said monitor comprises a flat monitor.

10. The apparatus according to claim 6 wherein said relative motion of said stationary target and said relatively moving background is selected from the group consisting of horizontal, spinning and rotational movement.

11. The apparatus according to claim 6 wherein the stationary target is not provided in a same plane as said moving background.

* * * * *